United States Patent [19]

Lunts et al.

[11] Patent Number: 4,959,381

[45] Date of Patent: Sep. 25, 1990

[54] PYRIDINE COMPOUNDS WHICH HAVE USEFUL ACTIVITY ASSOCIATED WITH REVERSIBLE AIR WAYS OBSTRUCTION

[75] Inventors: Lawrence H. C. Lunts, Broxbourne; Ian F. Skidmore, Welwyn; Harry Finch, Letchworth; Alan Naylor, Royston; Ian B. Campbell, Dane End, all of England

[73] Assignee: Glaxo Group Limited, London, England

[21] Appl. No.: 153,939

[22] Filed: Feb. 9, 1988

[30] Foreign Application Priority Data

Feb. 10, 1987 [GB] United Kingdom ................. 8703005
Feb. 10, 1987 [GB] United Kingdom ................. 8703006

[51] Int. Cl.$^5$ ............................................. A61K 31/44
[52] U.S. Cl. .................................... 514/357; 514/345; 514/351; 546/296; 546/300; 546/301; 546/302; 546/303; 546/329; 546/334
[58] Field of Search ............... 546/296, 300, 301, 302, 546/303, 329, 334; 514/345, 351, 357

[56] References Cited

FOREIGN PATENT DOCUMENTS

| | | | |
|---|---|---|---|
| 1445740 | 8/1976 | United Kingdom | 548/215 |
| 2088873 | 6/1982 | United Kingdom | 564/26 |
| 2140800 | 12/1984 | United Kingdom | 564/26 |
| 2159151 | 11/1985 | United Kingdom | 564/26 |
| 2165842 | 2/1986 | United Kingdom | 564/26 |
| 0220878 | 5/1987 | United Kingdom | 564/26 |

OTHER PUBLICATIONS

Chemical Abstracts, vol. 102, No. 17, Abstract 143,001m, Apr. 26, 1985, p. 38.
Chemical Abstracts, vol. 108, No. 11, Abstract 94,393d, Mar. 14, 1988, p. 94, 399.

Primary Examiner—Mary C. Lee
Assistant Examiner—Zinna Northington-Davis
Attorney, Agent, or Firm—Morgan & Finnegan

[57] ABSTRACT

The present invention provides compounds of the general formula (I)

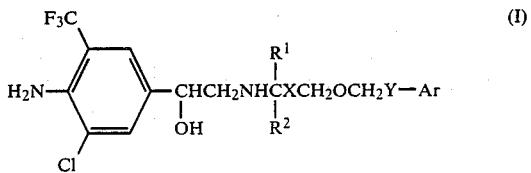

wherein

X represents a bond, or a $C_{1-6}$alkylene, $C_{2-6}$alkenylene or $C_{2-6}$alkynylene chain, and Y represents a bond, or a $C_{1-4}$alkylene, $C_{2-4}$alkenylene or $C_{2-4}$alkynylene chain with the proviso that the sum total of carbon atoms in X and Y is not more than 8;

$R^1$ and $R^2$ each represent a hydrogen atom or a $C_{1-3}$alkyl group, with the proviso that the sum total of carbon atoms in $R^1$ and $R^2$ is not more than 4; and Ar represents a pyridyl group optionally substituted by one or two substituents selected from halogen atoms or hydroxy, $C_{1-3}$alkyl and $C_{1-3}$alkoxy groups, or Ar represents a phenyl group optionally substituted by one or more substituents selected from halogen atoms or the groups hydroxy, hydroxy$C_{1-3}$alkyl, $C_{1-3}$alkyl, $C_{1-3}$alkoxy, $-NR^3R^4$ and $-NR^5COR^6$, or Ar is a phenyl group substituted by an alkylenedioxy group of formula $-O(CH_2)_pO-$; where $R^3$ and $R^4$ each represent a hydrogen atom or a $C_{1-4}$alkyl group or $-NR^3R^4$ forms a saturated heterocyclic amino group which has 5-7 ring members and optionally contains in the ring one or more atoms selected from $-O-$ and $-S-$ or a group $-NH-$ or $-N(CH_3)-$;

$R^5$ represents a hydrogen atom or a $C_{1-4}$alkyl group; $R^6$ represents a hydrogen atom or a $C_{1-4}$alkyl, $C_{1-4}$alkoxy, phenyl or $-NR^3R^4$ group;

p is an integer 1 or 2;

and physiologically acceptable salts and solvates (e.g. hydrates) thereof.

The compounds have a stimulant action at $\beta_2$-adreno receptors and may be used in the treatment of diseases associated with reversible airways obstruction such as asthma and chronic bronchitis.

12 Claims, No Drawings

PYRIDINE COMPOUNDS WHICH HAVE USEFUL ACTIVITY ASSOCIATED WITH REVERSIBLE AIR WAYS OBSTRUCTION

This invention relates to chloroaniline derivatives having a stimulant action $\beta_2$-adrenoreceptors, to processes for their preparation, to pharmaceutical compositions containing them and to their use in medicine.

Haloaniline derivatives have previously been described as having mimetic activity at $\beta_2$-adrenoreceptors and/or a blocking activity at $\beta_1$-adrenoreceptors.

Thus British Patent Specification No. 1445740 describes compounds of the general structure

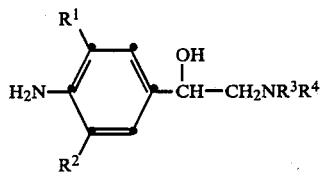

in which the substituent $R^1$ represents inter alia bromine or chlorine atoms; $R^2$ represents inter alia trifluoromethyl; $R^3$ and $R^4$ each represent hydrogen, $C_{1-6}$ alkyl, alkenyl, alkynyl, hydroxyalkyl, cycloalkyl, cycloalkylalkyl, or an optionally substituted aralkyl group. Such compounds have a mimetic activity at $\beta_2$-adrenoreceptors and/or a blocking activity at $\beta_1$-adrenoreceptors.

We have now found a novel group of chloroaniline derivatives, which differ structurally from those described in British Patent Specification No. 1445740, having a stimulant action at $\beta_2$-adrenoreceptors, and which have a desirable and useful profile of activity.

Thus the present invention provides compounds of the general formula (I)

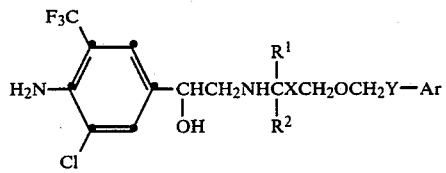

wherein

X represents a bond, or a $C_{1-6}$ alkylene, $C_{2-6}$ alkenylene or $C_{2-6}$ alkynylene chain and Y represents a bond, or a $C_{1-4}$ alkylene, $C_{2-4}$ alkenylene or $C_{2-4}$ alkynylene chain with the proviso that the sum total of carbon atoms in X and Y is not more than 8;

$R^1$ and $R^2$ each represent a hydrogen atom or a $C_{1-3}$ alkyl group, with the proviso that the sum total of carbon atoms in $R^1$ and $R^2$ is not more than 4; and Ar represents a pyridyl group optionally substituted by one or two substituents selected from halogen atoms or hydroxy, $C_{1-3}$ alkyl or $C_{1-3}$ alkoxy groups, or Ar represents a phenyl group optionally substituted by one or more substituents selected from halogen atoms or the groups hydroxy, hydroxy$C_{1-3}$alkyl, $C_{1-3}$ alkyl, $C_{1-3}$ alkoxy, —NR$^3$R$^4$ or —NR$^5$COR$^6$; or Ar is a phenyl group substituted by an alkylenedioxy group of formula —O(CH$_2$)$_p$O—; where $R^3$ and $R^4$ each represent a hydrogen atom or a $C_{1-4}$ alkyl group or —NR$^3$R$^4$ forms a saturated heterocyclic amino group which has 5–7 ring members and optionally contains in the ring one or more atoms selected from —O— or —S— or a group —NH— or —N(CH$_3$)—;

$R^5$ represents a hydrogen atom or a $C_{1-4}$ alkyl group;

$R^6$ represents a hydrogen atom or a $C_{1-4}$ alkyl, $C_{1-4}$ alkoxy, phenyl or —NR$^3$R$^4$ group;

p is an integer 1 or 2;

and physiologically acceptable salts and solvates (e.g. hydrates) thereof.

It will be appreciated that the compounds of general formula (I) possess one or two asymmetric carbon atoms, namely the carbon atom of the

group and, when $R^1$ and $R^2$ are different groups, the carbon atom to which these are attached. The compounds according to the invention thus include all enantiomers, diastereoisomers and mixtures thereof, including racemates. Compounds in which the carbon atom in the

group is in the R configuration are preferred.

In the definition of general formula (I), the term alkenylene includes both cis and trans structures.

In the general formula (I), the chain X may be for example a bond, —CH$_2$—, —(CH$_2$)$_2$—, —(CH$_2$)$_3$—, —(CH$_2$)$_4$—, —(CH$_2$)$_5$—, —(CH$_2$)$_6$—, —CH$_2$C≡C—, —(CH$_2$)$_2$CH=CH—, —(CH$_2$)$_2$C≡C—, —CH=CHCH$_2$—, —CH=CH(CH$_2$)$_2$— or —CH$_2$C≡CCH$_2$—. The chain Y may be for example a bond, —CH$_2$—, —(CH$_2$)$_2$—, —(CH$_2$)$_3$—, —(CH$_2$)$_4$—, —CH=CH—, —C≡C—, —CH$_2$CH=CH— or —CH$_2$C≡C—.

Preferably the total number of carbon atoms in the chains X and Y is 4 to 8 inclusive. Compounds wherein the sum total of carbon atoms in the chains X and Y is 4, 5, 6 or 7 are particularly preferred.

In one preferred group of compounds of formula (I) X represents a $C_{2-6}$ alkynylene or, more preferably, a $C_{1-6}$ alkylene chain and Y represents a $C_{1-4}$ alkylene chain. Particular compounds of this type are those wherein X is —(CH$_2$)$_3$— or —(CH$_2$)$_4$— and Y is —CH$_2$—, —(CH$_2$)$_2$— or —(CH$_2$)$_3$—, or X is —(CH$_2$)$_2$C≡C— and Y is —(CH$_2$)$_2$—.

In the compounds of formula (I) $R^1$ and $R^2$ may each be, for example, methyl, ethyl, propyl or isopropyl groups except that if one of $R^1$ and $R^2$ is a propyl or isopropyl group, the other is a hydrogen atom or a methyl group. $R^1$ and $R^2$ are each preferably a hydrogen atom or a methyl group.

A preferred group of compounds are those wherein $R^1$ and $R^2$ are both hydrogen atoms, or $R^1$ is a hydrogen atom and $R^2$ is a $C_{1-3}$ alkyl group, particularly a methyl group.

When Ar represents a pyridyl group this may be attached to the rest of the molecule at either the 2-, 3- or 4-position.

When the pyridyl group is substituted, the substituent(s) may be at the 2-, 3-, 4-, 5- or 6- position(s) in the ring. When the pyridyl group is substituted by one or two halogen atoms, these may be fluorine, chlorine or, more preferably, bromine. When the pyridyl group is substituted, it preferably contains a single substituent.

More preferably the substituted pyridyl group is attached to the rest of the molecule at the 2- position, and the single substituent is at the 3-, 5- or 6- position.

A preferred group of compounds are those of formula (I) in which Ar represents an optionally substituted pyridyl group, and more especially a pyridyl group attached to the rest of the molecule at the 2-, 3- or 4- position, and optionally containing a single substituent selected from hydroxy, $C_{1-3}$ alkyl (e.g. methyl), $C_{1-3}$ alkoxy (e.g. methoxy) or halogen (e.g. bromine). Within this group particularly preferred compounds are those in which Ar is an unsubstituted pyridyl group.

When Ar represents a phenyl group substituted by one or more halogen atoms, these may be chlorine, bromine, fluorine or iodine.

When —$NR^3R^4$ in compounds of formula (I) represents a saturated heterocyclic amino group this may have 5, 6 or 7 ring members and optionally contains in the ring a heteroatom selected from —O— or —S—, or a group —NH— or —N($CH_3$)—. Examples of such —$NR^3R^4$ groups are pyrrolidino, piperidino, hexamethyleneimino, piperazino, N-methylpiperazino, morpholino, homomorpholino or thiamorpholino.

The phenyl group Ar may optionally contain one, two or three substituents, which may be at the 2-, 3-, 4-, 5- or 6- position(s) in the ring. Particular examples of a disubstituted phenyl group represented by Ar include phenyl substituted by two hydroxyl groups (e.g. 3,5-dihydroxyphenyl).

In one preferred group of compounds of formula (I) Ar represents a phenyl group optionally substituted by a fluorine atom, a group selected from amino, $C_{1-3}$ alkyl (e.g. methyl), $C_{1-3}$ alkoxy (e.g. methoxy), hydroxy $C_{1-2}$ alkyl (e.g. hydroxymethyl), morpholino, hydroxy or —$NHCOR^6$ where $R^6$ is $C_{1-3}$ alkyl (e.g. methyl), or Ar is a phenyl group substituted by hydroxyl groups at the 3- and 5-positions or Ar represents a pyridyl group attached to the rest of the molecule at the 2-, 3- or 4- position, optionally containing a single substituent selected from hydroxy, $C_{1-3}$ alkyl (e.g. methyl), $C_{1-3}$ alkoxy (e.g. methoxy) or halogen (e.g. bromine). Within this group, compounds where Ar is an unsubstituted phenyl group are particularly preferred. A further preferred group of compounds are those of formula (I) wherein X represents a $C_{3-4}$ alkylene or $C_3$ alkynylene chain;
Y represents a $C_{1-4}$ alkylene chain;
$R^1$ and $R^2$ each represent hydrogen; and Ar represents a phenyl group optionally substituted by a fluorine atom, a group selected from amino, $C_{1-3}$ alkyl (e.g. methyl), $C_{1-3}$ alkoxy (e.g. methoxy), hydroxy $C_{1-2}$ alkyl (e.g. hydroxymethyl), morpholino, hydroxy or —$NHCOR^6$ where $R^6$ is $C_{1-3}$ alkyl (e.g. methyl), or Ar is a phenyl group substituted by hydroxyl groups at the 3-and 5- positions or Ar represents a pyridyl group attached to the rest of the molecule at the 2-, 3- or 4- position, optionally containing a single substituent selected from hydroxy, $C_{1-3}$ alkyl (e.g. methyl), $C_{1-3}$ alkoxy (e.g. methoxy) or halogen (e.g. bromine); and physiologically acceptable salts and solvates thereof.

Especially preferred compounds from within this group are those in which Ar is an unsubstituted pyridyl group attached to the rest of the molecule at the 2- position, or Ar is an unsubstituted phenyl group.

Preferred compounds according to the invention are:
4-amino-3-chloro-α-[[[5-(2-phenylethoxy)pentyl]amino]methyl]-5-(trifluoromethyl)benzenemethanol,
4-amino-3-chloro-α-[[[6-[2-(2-pyridinyl)ethoxy]-hexyl]amino]methyl]-5-(trifluoromethyl)benzenemethanol, and their physiologically acceptable salts and solvates.

Suitable physiologically acceptable salts of the compounds of general formula (I) include acid addition salts derived from inorganic and organic acids, such as hydrochlorides, hydrobromides, sulphates, phosphates, maleates, tartrates, citrates, benzoates, 4-methoxybenzoates, 2- or 4-hydroxybenzoates, 4-chlorobenzoates, benzenesulphonates, p-toluenesulphonates, methanesulphonates, naphthalenesulphonates, sulphamates, ascorbates, salicylates, acetates, diphenylacetates, triphenylacetates, adipates, fumarates, succinates, lactates, glutarates, gluconates, tricarballylates, hydroxynaphthalenecarboxylates (e.g. 1-hydroxy- or 3-hydroxy-2-naphthalenecarboxylates), or oleates. The compounds may also form salts with suitable bases. Examples of such salts are alkali metal (e.g. sodium or potassium) and alkaline earth metal (e.g. calcium or magnesium) salts.

The compounds according to the invention have a stimulant action at $\beta_2$-adrenoreceptors, which furthermore is of a particularly advantageous profile. The stimulant action may be demonstrated in the isolated trachea of the guinea-pig, where such compounds cause relaxation of contractions induced by $PGF_{2\alpha}$ or electrical stimulation. A particularly long duration of action has also been observed.

The compounds according to the invention may be used in the treatment of diseases associated with reversible airways obstruction such as asthma and chronic bronchitis.

The compounds according to the invention are also indicated as useful for the treatment of inflammatory and allergic skin diseases, congestive heart failure, depression, premature labour, glaucoma, and in the treatment of conditions in which there is an advantage in lowering gastric acidity, particularly in gastric and peptic ulceration.

The invention accordingly further provides compounds of formula (I) and their physiologically acceptable salts and solvates for use in the therapy or prophylaxis of diseases associated with reversible airways obstruction in human or animal subjects.

The compounds according to the invention may be formulated for administration in any convenient way. The invention therefore includes within its scope pharmaceutical compositions comprising at least one compound of formula (I) or a physiologically acceptable salt or solvate thereof formulated for use in human or veterinary medicine. Such compositions may be presented for use with physiologically acceptable carriers or excipients, optionally with supplementary medicinal agents.

The compounds may be formulated in a form suitable for administration by inhalation or insufflation, or for oral, buccal, parenteral, topical (including nasal) or rectal administration. Administration by inhalation or insufflation is preferred.

For administration by inhalation the compounds according to the invention are conveniently delivered in the form of an aerosol spray presentation from pressurised packs, with the use of a suitable propellant, such as dichlorodifluoromethane, trichlorofluoromethane, dichlorotetrafluoroethane, carbon dioxide or other suitable gas, or from a nebuliser. In the case of a pressurised aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in for example capsules or cartridges of e.g. gelatin, or blister packs from which the powder may be administered with the aid of an inhaler or insufflator.

For oral administration, the pharmaceutical composition may take the form of, for example, tablets, capsules, powders, solutions, syrups or suspensions prepared by conventional means with acceptable excipients.

For buccal administration the composition may take the form of tablets, drops or lozenges formulated in conventional manner.

The compounds of the invention may be formulated for parenteral administration by bolus injection or continuous infusion. Formulations for injection may be presented in unit dosage form in ampoules, or in multi-dose containers with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for reconstitution with a suitable vehicle, e.g. sterile pyrogen-free water, before use.

For topical administration the pharmaceutical composition may take the form of ointments, lotions or creams formulated in a conventional manner, with for example an aqueous or oily base, generally with the addition of suitable thickening agents and/or solvents. For nasal application, the composition may take the form of a spray, formulated for example as an aqueous solution or suspension or as an aerosol with the use of a suitable propellant.

The compounds of the invention may also be formulated in rectal compositions such as suppositories or retention enemas, e.g. containing conventional suppository bases such as cocoa butter or other glyceride.

Where pharmaceutical compositions are described above for oral, buccal, rectal or topical administration, these may be presented in a conventional manner associated with controlled release forms.

A proposed daily dosage of active compound for the treatment of man is 0.005 mg to 100 mg, which may be conveniently administered in one or two doses. The precise dose employed will of course depend on the age and condition of the patient and on the route of administration. Thus a suitable dose for administration by inhalation is 0.005 mg to 20 mg, for oral administration is 0.02 mg to 100 mg, and for parenteral administration is 0.01 mg to 2 mg for administration by bolus injection and 0.01 mg to 25 mg for administration by infusion.

The compounds according to the invention may be prepared by a number of processes. In the following description X, Y, Ar, $R^1$ and $R^2$ are as defined for general formula (I) unless otherwise specified. In the preparation of both intermediates and end-products the final step in the reaction may be the removal of a protecting group. Suitable protecting groups and their removal are described in general process (2) below.

In one general process (1) compounds of formula (I) may be prepared by reducing an intermediate of general formula (II):

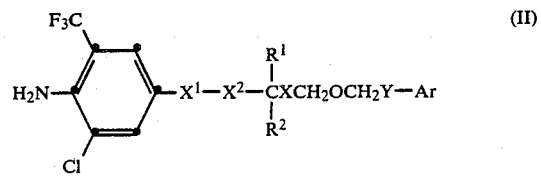

(II)

wherein at least one of $X^1$ and $X^2$ represents a reducible group and the other takes the appropriate meaning as follows, which is $X^1$ is —CH(OH)— and $X^2$ is —CH$_2$N-$R^7$— (where $R^7$ represents a hydrogen atom or a protecting group), followed where necessary by removal of any protecting groups.

Suitable reducible groups include those wherein $X^1$ is a group

and $X^2$ is a group —CH$_2$NR$^8$— (wherein $R^8$ represents a group convertible to hydrogen by catalytic hydrogenation, for example an arylmethyl group such as benzyl, benzhydryl or α-methylbenzyl).

The reduction may be effected using reducing agents conveniently employed for the reduction of ketones or protected amines.

Thus, for example, when $X^1$ in general formula (II) represents a

group this may be reduced to a —CH(OH)— group using hydrogen in the presence of a catalyst such as platinum, platinum oxide, palladium, palladium oxide, Raney nickel or rhodium, on a support such as charcoal, using an alcohol e.g. ethanol, an ester e.g. ethyl acetate, an ether e.g. tetrahydrofuran, or water, as reaction solvent, or a mixture of solvents, e.g. a mixture of two or more of those just described, at normal or elevated temperature and pressure, for example from 20° to 100° C. and from 1 to 10 atmospheres. Alternatively, the reducing agent may be, for example, a hydride such as diborane or a metal hydride such as lithium aluminium hydride, sodium bis(2-methoxyethoxy) aluminium hydride, sodium borohydride or aluminium hydride. The reaction may be effected in a solvent, where appropriate an alcohol e.g. methanol or ethanol, or an ether such as tetrahydrofuran, or an halogenated hydrocarbon such as dichloromethane.

When $X^2$ in general formula (II) represents a —CH$_2$NR$^8$— group, this may be reduced to a —CH$_2$NH— group using hydrogen in the presence of a catalyst as described above.

Where it is desired to use a protected intermediate of general formula (II) it is particularly convenient to use a protecting group $R^7$ which is capable of being removed under the reducing conditions, for example hydrogen and a catalyst, thus avoiding the need for a separate deprotection step. Suitable protecting groups of this type include arylmethyl groups such as benzyl, benzhydryl and α-methylbenzyl.

In the above reduction process, and also in the preparation of intermediates, care must be taken to avoid the use of hydrogen and a catalyst when products are required in which X and/or Y represent alkenylene or alkynylene groups.

In a further process (2) compounds of formula (I) may be prepared by deprotecting a protected intermediate of general formula (III)

$$\text{F}_3\text{C} \diagdown \underset{\text{Cl}}{\overset{}{\bigcirc}} \diagup \text{CHCH}_2\text{NR}^7\overset{\text{R}^1}{\underset{\text{R}^2}{\text{C}}}\text{XCH}_2\text{OCH}_2\text{Y}-\text{Ar} \quad \text{(III)}$$
$$\text{H}_2\text{N}- \qquad \qquad \overset{|}{\text{OH}}$$

(wherein R⁷ is a protecting group).

The protecting group may be any conventional protecting group as described for example in "Protective Groups in Organic Chemistry", by Theodora Greene (John Wiley and Sons Inc, 1981). Examples of suitable amino protecting groups represented by R⁷ are arylmethyl groups such as benzyl, α-methylbenzyl, diphenylmethyl or triphenylmethyl, and acyl groups such as acetyl, trichloroacetyl or trifluoroacetyl.

The deprotection to yield a compound of general formula (I) may be effected using conventional techniques. Thus for example arylmethyl groups may be removed by hydrogenolysis in the presence of a metal catalyst (e.g. palladium on charcoal). Acyl groups may be removed by hydrolysis with a base such as sodium hydroxide or potassium carbonate, or a group such as trichloroacetyl or trifluoroacetyl may be removed by reduction with, for example, zinc and acetic acid.

Intermediates of formula (II) for use in the reduction process (1) in which X¹ is a group $$\diagdown \text{C}=\text{O} \diagup$$

may be prepared from a haloketone of formula (IV)

$$\text{F}_3\text{C} \diagdown \bigcirc \diagup \text{COCH}_2\text{Hal} \quad \text{(IV)}$$
$$\text{H}_2\text{N}-$$
$$\text{Cl}$$

(where Hal represents a halogen atom e.g. bromine) by reaction with an amine of general formula (V)

$$\text{R}^9\text{NHC}\overset{\text{R}^1}{\underset{\text{R}^2}{\text{X}}}\text{CH}_2\text{OCH}_2\text{Y}-\text{Ar} \quad \text{(V)}$$

(where R⁹ is a hydrogen atom or a group convertible thereto by catalytic hydrogenation).

The reaction may be effected in a cold or hot solvent, for example tetrahydrofuran, tert-butyl methyl ether, dioxan, chloroform, dichloromethane, dimethylformamide, acetonitrile, a ketone such as butanone or methylisobutylketone, or an ester such as ethyl acetate, preferably in the presence of a base such as diisopropylethylamine, sodium carbonate or other acid scavenger such as propylene oxide.

Intermediates of general formula (II) in which X¹ is a group $$\diagdown \text{C}=\text{O} \diagup$$

may be reduced to the corresponding intermediate in which X¹ is a group —CH(OH)— using for example a metal hydride such as sodium borohydride in a solvent e.g. ethanol, methanol and/or tetrahydrofuran.

Intermediates of formula (IV) are either known compounds or may be prepared by methods analogous to those described for the preparation of known compounds.

Suitable methods for preparing intermediates of formula (V) are described in UK Patent Specifications Nos. 2140800A and 2159151A and in the exemplification included hereinafter.

In the general processes described above, the compound of formula (I) obtained may be in the form of a salt, conveniently in the form of a physiologically acceptable salt. Where desired, such salts may be converted to the corresponding free bases using conventional methods.

Physiologically acceptable salts of the compounds of general formula (I) may be prepared by reacting a compound of general formula (I) with an appropriate acid or base in the presence of a suitable solvent such as acetonitrile, acetone, chloroform, ethyl acetate or an alcohol, e.g. methanol, ethanol or iso-propanol.

Physiologically acceptable salts may also be prepared from other salts, including other physiologically acceptable salts, of the compounds of general formula (I), using conventional methods.

When a specific enantiomer of a compound of general formula (I) is required, this may be obtained by resolution of a corresponding racemate of a compound of general formula (I) using conventional methods.

Thus, in one example an appropriate optically active acid may be used to form salts with the racemate of a compound of general formula (I). The resulting mixture of isomeric salts may be separated for example by fractional crystallisation, into the diastereoisomeric salts from which the required enantiomer of a compound of general formula (I) may be isolated by conversion into the required free base.

Alternatively, enantiomers of a compound of general formula (I) may be synthesised from the appropriate optically active intermediates using any of the general processes described herein.

Specific diastereoisomers of a compound of formula (I) may be obtained by conventional methods for example, by synthesis from an appropriate asymmetric starting material using any of the processes described herein, or by conversion of a mixture of isomers of a compound of general formula (I) into appropriate diastereoisomeric derivatives e.g. salts which then can be separated by conventional means e.g. by fractional crystallisation.

The following examples illustrate the invention. Temperatures are in °C. 'Dried' refers to drying using sodium sulphate. Thin layer chromatography (t.l.c.) was carried out on silica and flash column chromatography (FCC) was carried out on silica (Merck 9385).

INTERMEDIATE 1

N-[5-(2-Phenylethoxy)pentyl]benzenemethanamine

[2-[(5-Bromopentyl)oxy]ethyl]benzene (10.0 g) was added over 1 h to benzylamine (30 ml) at ca. 120° under nitrogen. After 2 h at 120° the reaction mixture was added to 2N hydrochloric acid (200 ml), the mixture was extracted with ethyl acetate (2×250 ml) and the combined organic extracts were washed with 2N sodium carbonate, water and brine, dried and concentrated in vacuo to give the title compound as a pale yellow oil (8.6 g), t.l.c. (ethyl acetate-triethylamine 99:1) Rf 0.78

INTERMEDIATE 2

4-Amino-3-chloro-α-[[[5-(2-phenylethoxy)pentyl](phenylmethyl)amino]methyl]-5-(trifluoromethyl)benzenemethanol 1-[4-Amino-3-chloro-5-(trifluoromethyl)phenyl]-2-bromoethanone (0.55 g), N-[5-(2-phenylethoxy)pentyl]benzenemethanamine (0.52 g) and N,N-diisopropylethylamine (0.25 g) were stirred in tetrahydrofuran (15 ml) at room temperature under nitrogen for 40 h. The mixture was filtered and the filtrate evaporated in vacuo. The residue was dissolved in methanol (20 ml) and sodium borohydride (0.18 g) was added portionwise to the stirred solution at 0° under nitrogen. The mixture was left to stand at room temperature under nitrogen overnight, 2N hydrochloric acid (10 ml) added and the solvent evaporated in vacuo. The residue was partitioned between 8% sodium bicarbonate (100 ml) and ethyl acetate (100 ml), the organic phase separated, dried and evaporated in vacuo to give an oil. Purification by FCC on triethylamine deactivated silica (Merck 9385) eluting with cyclohexane-ethyl acetate (9:1) gave the title compound as a colourless oil (0.5 g).

Analysis found: C,59.2; H,6.3; N,6.3.
$C_{22}H_{28}ClF_3N_2O$ requires C,59.4; H,6.3; N,6.3%.

INTERMEDIATE 3

2-[2-[(6-Bromohexyl)oxy]ethyl]pyridine

A mixture of 2-pyridineethanol (5 g), 1,6-dibromohexane (20 ml), 50% (w/v) sodium hydroxide (20 ml) and tetra-n-butylammonium hydrogen sulphate (500 mg) was stirred at room temperature for 6 h, Water (100 ml) was added and the mixture was extracted with ether (2×100 ml). The organic extracts were washed with water and brine, dried and concentrated to an oil which was purified by FCC eluting with hexane→hexane-ether(1:1) to give the title compound as a colourless oil (6.6 g), t.l.c. (hexane-ether 1:1) Rf 0.19.

INTERMEDIATE 4

N-[6-[2-(2-Pyridinyl)ethoxy]hexyl]benzenemethanamine

2-[2-[(6-Bromohexyl)oxy]ethyl]pyridine (6.3 g) was added to benzylamine (20 ml) at 140° under nitrogen. After 1 h at 140° the reaction mixture was cooled and partitioned between 2M sodium hydroxide (100 ml) and ether (100 ml). The organic layer was washed with water and brine, dried and concentrated to a yellow oil. The excess benzylamine was removed by distillation under reduced pressure to leave the title compound as a yellow oil (6.8 g), t.l.c. (toluene-ethanol-0.88 ammonia 80:20:2) Rf 0.44.

INTERMEDIATE 5

4-Amino-3-chloro-α-[[(phenylmethyl)[6-[2-(2-pyridinyl)ethoxy]hexyl]amino]methyl]-5-(trifluoromethyl)benzenemethanol 1-[4-Amino-3-chloro-5-(trifluoromethyl)phenyl]-2-bromoethanone (2.1 g), N-[6-[2-(2-pyridinyl)ethoxy]hexyl]benzenemethanamine (2.20 g) and N,N-diisopropylethylamine (0.94 g) were stirred together in tetrahydrofuran (45 ml) for 24 h at room temperature under nitrogen. The mixture was filtered and the filtrate evaporated in vacuo. The residue was dissolved in methanol (80 ml) and sodium borohydride (0.63 g) was added portionwise to the solution at 0° under nitrogen. The mixture was stirred for 1 h and then 2N hydrochloric acid (40 ml) was added. The solvent was evaporated in vacuo, the residue partitioned between 8% sodium bicarbonate solution (150 ml) and ethyl acetate (100 ml). The organic phase was separated, and the aqueous phase re-extracted with ethyl acetate (100 ml). The combined organic extracts were dried and evaporated in vacuo to give a yellow oil. Purification by FCC eluting with toluene-ethanol-triethylamine (98:2:1) afforded the title compound as a yellow oil (1.59 g).

Analysis Found: C,63.5; H,6.4; N,7.9; Cl,6.8.
$C_{29}H_{35}ClF_3N_3O_2$ requires C,63.6; H,6.1; N,7.7; Cl,6.5%.

EXAMPLE 1

4-Amino-3-chloro-α-[[[6-(2-pyridinylethoxy)hexyl]amino]methyl]-5-(trifluoromethyl)benzenemethanol A solution of 4-amino-3-chloro-α-[[(phenylmethyl)[6-(2-pyridinylethoxy)hexyl]amino]methyl]-5-(trifluoromethyl)benzenemethanol (1.50 g) in absolute ethanol (10 ml) and conc. hydrochloric acid/ethanol (1:9 v/v, 2.48 ml) was hydrogenated over pre-reduced 10% palladium oxide on charcoal (50% aqueous, 300 mg) in absolute ethanol (10 ml). The mixture was filtered through hyflo and evaporated in vacuo to give an oil. Purification by FCC eluting with toluene-ethanol-triethylamine (95:5:1) gave a pink oil. Trituration with hexane afforded the title compound as a pale orange solid (0.87 g), m.p. 51.5°–53°.

Analysis Found: C,57.1; H,6.5; N,8.9.
$C_{22}H_{29}ClF_3N_3O_2$ requires C,57.4; H,6.4; N,9.1%.

EXAMPLE 2

4-Amino-3-chloro-α-[[[5-(2-phenylethoxy)pentyl]amino]methyl]-5-(trifluoromethyl)benzenemethanol A solution of 4-amino-3-chloro-α-[[[5-(2-phenylethoxy)pentyl](phenylmethyl)amino]methyl]-5-(trifluoromethyl)benzenemethanol (0.42 g) and conc. hydrochloric acid/ethanol (1:9 v/v, 0.71 ml) was hydrogenated over pre-reduced 10% palladium oxide on charcoal (80 mg, 50% aqueous paste) in absolute ethanol (5 ml). The mixture was filtered through hyflo and evaporated in vacuo to give an oil which was purified by FCC eluting with toluene-ethanol-triethylamine (95:5:1) to give the title compound as a white solid (0.22 g) m.p. 70°–71.5°.

Analysis Found: C,59.2; H,6.3; N,6.3; Cl,8.1.
$C_{22}H_{28}ClF_3N_2O_2$ requires C,59.4; H,6.3; N,6.3; Cl,8.0%.

The following are examples of suitable formulations of compounds of the invention. The term 'active ingre- 'dient' is used herein to represent a compound of the invention.

|  | mg/tablet |
|---|---|
| Active ingredient | 2.0 |
| Microcrystalline cellulose USP | 196.5 |
| Magnesium Stearate BP | 1.5 |
| Compression weight | 200.0 |

The active ingredient is sieved through a suitable sieve, blended with the excipients and compressed using 7 mm diameter punches.

Tablets of other strengths may be prepared by altering the ratio of active ingredient to microcrystalline cellulose or the compression weight and using punches to suit.

The tablets may be film coated with suitable film forming materials, such as hydroxypropylmethylcellulose, using standard techniques. Alternatively, the tablets may be sugar coated.

| Metered Dose Pressurised Aerosol (Suspension Aerosol) | | |
|---|---|---|
|  | mg/metered dose | Per can |
| Active ingredient micronised | 0.100 | 26.40 mg |
| Oleic Acid BP | 0.100 | 2.64 mg |
| Trichlorofluoromethane BP | 23.64 | 5.67 g |
| Dichlorodifluoromethane BP | 61.25 | 14.70 g |

The active ingredient is micronised in a fluid energy mill to a fine particle size range. The oleic acid is mixed with the trichlorofluoromethane at a temperature of 10°–15° C. and the micronised drug is mixed into the solution with a high shear mixer. The suspension is metered into aluminium aerosol cans and suitable metering valves delivering 85 mg of suspension are crimped onto the cans and the dichlorodifluoromethane is pressure filled into the cans through the valves.

| Inhalation Cartridges | mg/cartridge |
|---|---|
| Active ingredient micronised | 0.200 |
| Lactose BP to | 25.0 |

The active ingredient is micronised in a fluid energy mill to a fine particle size range prior to blending with normal tabletting grade lactose in a high energy mixer. The powder blend is filled into No. 3 hard gelatin capsules on a suitable encapsulating machine. The contents in the cartridges are administered using a powder inhaler such as the Glaxo Rotahaler.

We claim:

1. A compound of formula (I)

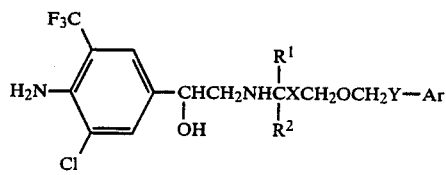

wherein

X represents a bond, or a $C_{1-6}$ alkylene, $C_{2-6}$ alkenylene or $C_{2-6}$ alkynylene chain, and Y represents a bond, or a $C_{1-4}$ alkylene, $C_{2-4}$ alkenylene or $C_{2-4}$ alkynylene chain, where the sum total of carbon atoms in X and Y is from 1 to 8;

$R^1$ and $R^2$ each represent a hydrogen atom or a $C_{1-3}$ alkyl group, where the sum total of carbon atoms in $R^1$ and $R^2$ is from 1 to 4; and Ar represents a pyridyl group optionally substituted by one or two substituents selected from halogen atoms or hydroxy, $C_{1-3}$ alkyl and $C_{1-3}$ alkoxy groups or a physiologically acceptable salt or solvate thereof.

2. A compound according to claim 1 in which the sum total of carbon atoms in the chains —X and —Y is 4, 5, 6 or 7.

3. A compound according to claim 1 in which —X— is —(CH$_2$)$_3$— or —(CH$_2$)$_4$ and Y is —CH$_2$—, —(CH$_2$)$_2$— or —(CH$_2$)$_3$— or X is —(CH$_2$)$_2$C≡C— and Y is —(CH$_2$)$_2$—.

4. A compound according to claim 1 in which $R^1$ and $R^2$ are both hydrogen atoms, or $R^1$ is a hydrogen atom and $R^2$ is a $C_{1-3}$ alkyl group.

5. A compound according to claim 1, in which Ar represents a pyridyl group attached to the rest of the molecule at the 2-, 3-, or 4- position optionally containing a single substituent selected from hydroxy, $C_{1-3}$ alkyl, $C_{1-3}$ alkoxy or halogen.

6. A compound according to claim 1 in which

X represents a $C_{3-4}$ alkylene or $C_3$ alkynylene chain;

Y represents a $C_{1-4}$ alkylene chain;

$R^1$ and $R^2$ each represent hydrogen; and

Ar represents a pyridyl group attached to the rest of the molecule at the 2-, 3- or 4- position, optionally containing a single substituent selected from hydroxy, $C_{1-3}$ alkyl, $C_{1-3}$ alkoxy or halogen.

7. A compound according to claim 6 in which Ar is an unsubstituted pyridyl group attached to the rest of the molecule at the 2- position.

8. A compound which is 4-amino-3-chloro-α-[[[6-[2-(2-pyridinyl)ethoxy]hexyl]amino]methyl]-5-(trifluoromethyl)benzenemethanol or a physiologically acceptable salt or solvate solvates thereof.

9. A pharmaceutical composition for therapy or prophylaxis of a disease associated with reversible airways obstruction which comprises an effective amount to alleviate said disease of at least one compound of formula (I) as defined in claim 1 or a physiologically acceptable salt or solvate thereof, together with a physiologically acceptable carrier or excipient.

10. A method of therapy or prophylaxis of a disease associated with reversible airways obstruction in a patient which comprises administering to said patient an effective amount to alleviate said disease of a compound of formula (I) as defined in claim 1 or a physiologically acceptable salt or solvate thereof.

11. A pharmaceutical composition of claim 9 wherein the disease associated with reversible airways obstruction is asthma or chronic bronchitis.

12. A method of claim 10 wherein the disease associated with reversible airways obstruction is asthma or chronic bronchitis.

* * * * *